US00PP15737P2

(12) United States Plant Patent
Lim et al.

(10) Patent No.: US PP15,737 P2
(45) Date of Patent: Apr. 26, 2005

(54) SHRUB ROSE PLANT NAMED 'BAICKER'

(50) Latin Name: *Rosa hybrida*
Varietal Denomination: BAIcker

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 39 days.

(21) Appl. No.: 10/796,095

(22) Filed: Mar. 10, 2004

(51) Int. Cl.[7] ..... A01H 5/00
(52) U.S. Cl. ..... Plt./102
(58) Field of Search ..... Plt./102

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct variety of landscape shrub rose plant is provided which forms on a recurrent basis in clusters attractive single rich red blossoms suffused with rosy pink having a near white to yellow eye. The plant exhibits a compact, upright and bushy growth habit, glossy medium green foliage, and excellent tolerance to Black Spot and Powdery Mildew. The attractive medium green glossy foliage contrasts nicely with the red blossom coloration. A tough rose plant of good hardiness is provided. The plant can be grown to advantage as a specimen, border planting, or as a mass planting.

2 Drawing Sheets

Botanical commercial classification: *Rosa hybrida*/Shrub Rose Plant.
Varietal denomination: cv. 'BAIcker'.

SUMMARY OF THE INVENTION

The new variety of *Rosa hybrida* landscape shrub rose plant was created at Yamhill, Oreg. during 1993 by artificial pollination wherein two parents were crossed which previously had been studied in the hope that they would contribute the desired characteristics. The female parent (i.e., the seed parent) was the 'Meipitac' variety (U.S. Plant Pat. No. 7,783). The male parent (i.e., the pollen parent) was the 'Chuckles' variety (U.S. Plant Pat. No. 1,608). The 'Meipitac' variety is marketed under the CAREFREE WONDER trademark. The parentage of the new variety can be summarized as follows:

'Meipitac'×'Chuckles'.

The seeds resulting from the above pollination were sown and plants were obtained which were physically and biologically different from each other. Selective study resulted in the identification during 1996 of a single plant of the new variety having the distinctive ornamental characteristics hereafter described.

It was found that the new variety of the present invention:

(a) exhibits a compact, upright and bushy growth habit,
(b) forms recurrently in clusters attractive rich medium red blossoms suffused with rosy pink having a near white to yellow eye,
(c) forms glossy medium green adult foliage,
(d) displays excellent tolerance to Black Spot and Powdery Mildew; and
(e) is particularly well suited for growing as attractive ornamentation in parks and gardens.

The red-purple buds open to rich medium red to light pink blooms that contrast nicely with the medium green glossy foliage. A tough shrub rose plant having good hardiness is provided.

The new variety well meets the needs of the horticultural industry. It can be grown to advantage anywhere in the landscape where attractive ornamentation is desired. The distinctive blossoms are displayed throughout the summer on a recurrent bloom cycle. The plant can be grown as a specimen, border planting, or as a mass ground cover.

The new variety can be readily distinguished from its parental varieties. More specifically, the 'Meipitac' variety forms pink double blossoms having approximately 26 petals, and the 'Chuckles' variety is a Floribunda rose that forms deep pink blossoms.

Additionally, the new variety can be readily distinguished from 'Nearly Wild' variety (non-patented in the United States) and the 'KORgosa' variety (non-patented in the United States). More specifically, the 'Nearly Wild' plant commonly assumes a taller height of approximately 80 cm at the end of the growing season, and forms larger blossoms having a diameter of approximately 9 cm that are medium rose pink on the observe and light pink on the reverse and comprise only five petals. The 'KORgosa' plant commonly assumes a much taller height of approximately 1.65 m at the end of the growing season, and forms smaller blossoms having a diameter of approximately 6.5 cm that are deep red with a white eye on the obverse and medium red on the reverse and comprise only five petals. The 'KORgosa' variety sometimes is known as the 'Robusta' variety.

The new variety has been found to undergo asexual propagation by budding on an understock beginning in April 1994 and by the rooting of cuttings. 'Dr. Huey' rootstock was used during the budding. Such asexual propagation by these techniques at Yamhill, Oreg., St. Paul, Minn., and at Phoenix, Ariz. has shown that the characteristics of the new variety are stable and are strictly transmissible by such asexual propagation from one generation to another. The new variety grows well on its own roots.

Initially the new plant was designated 93H42-1P. The new variety subsequently has been named the 'BAIcker' variety, and currently is being marketed while using the GARDEN JUBILEE and FIRECRACKER trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors at St. Paul, Minn. and at Yamhill, Oreg. during the seasons of 2002 and 2003.

DETAILED DESCRIPTION

Figure 1:
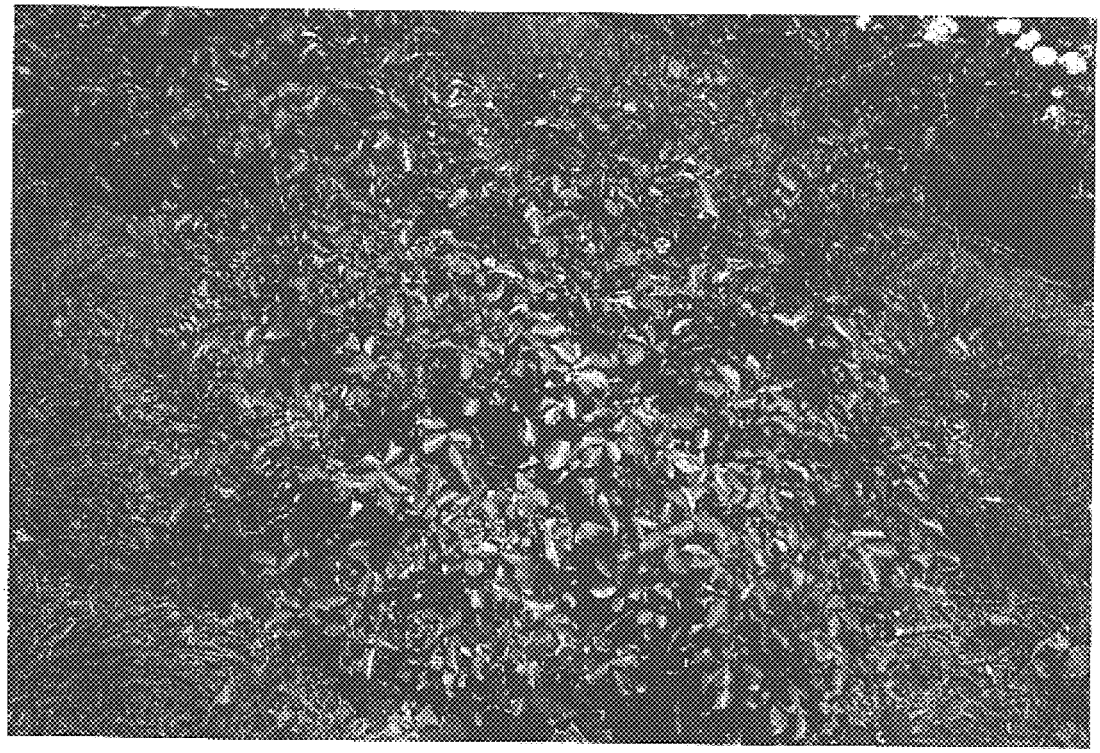
FIG. 1 illustrates typical plants with blossoms in various stages of opening and foliage of the new variety.
Figure 2:
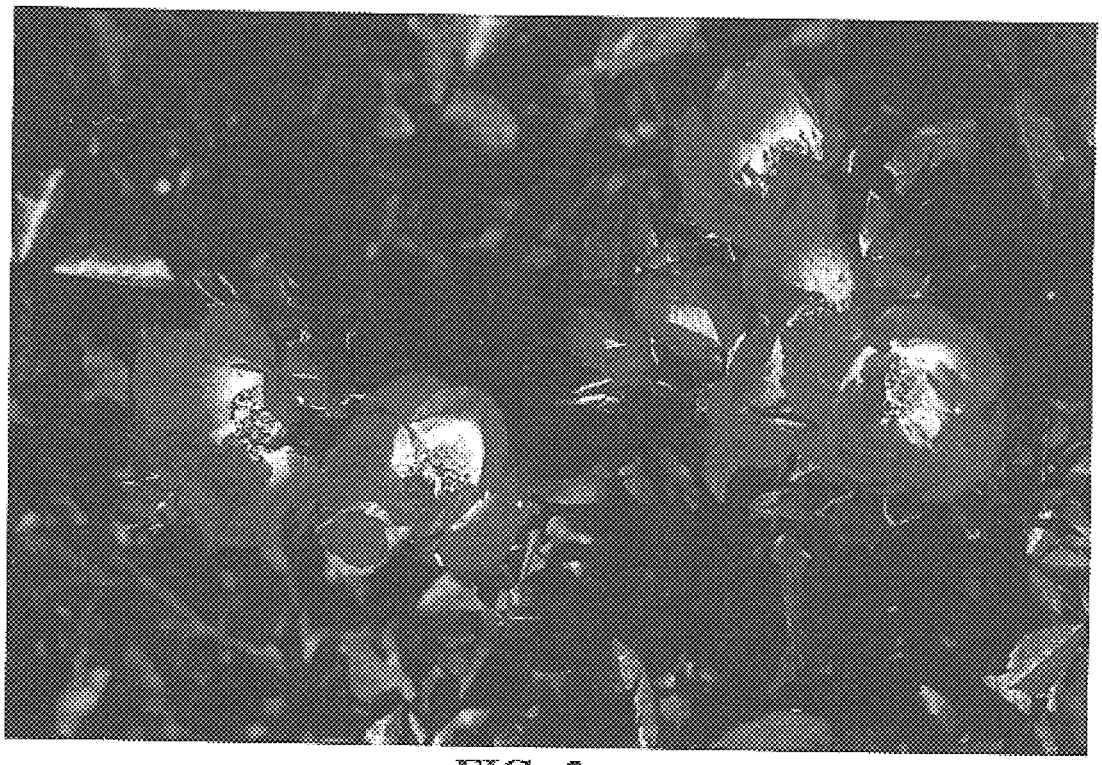
FIG. 2 illustrates a closer view of typical buds and fully open flowers of the new variety in greater detail.
Figure 3:
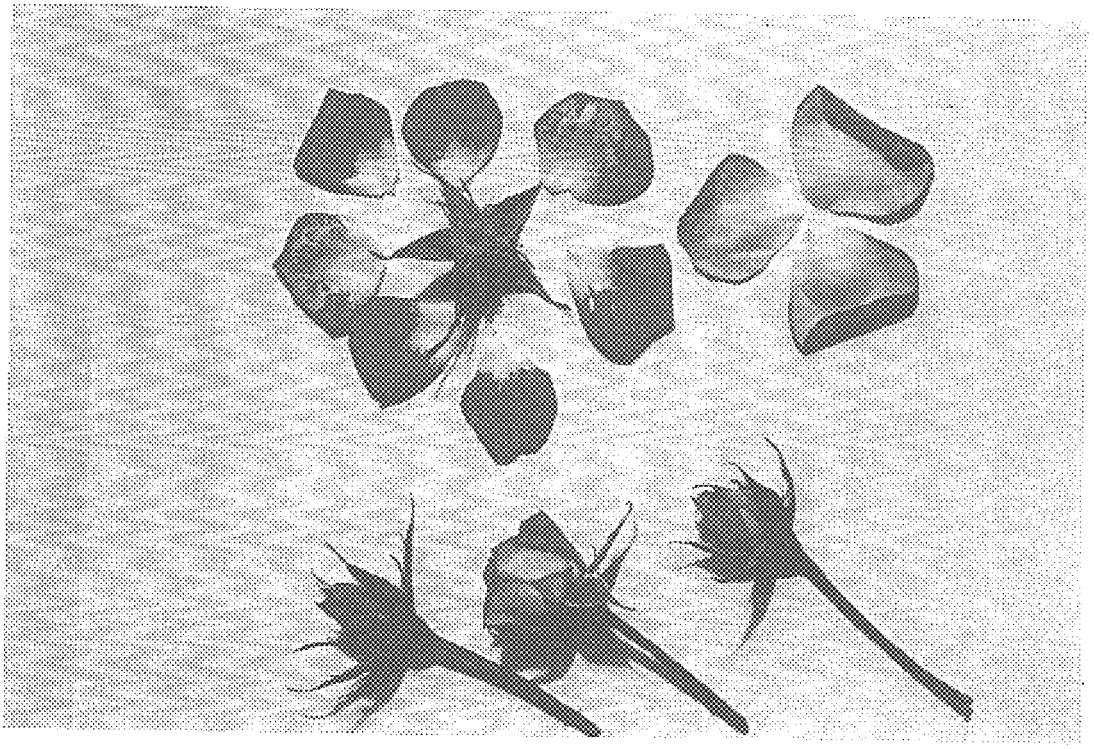
FIG. 3 illustrates at the top typical blossom petals with the upper surfaces being shown at the left and the under surfaces being shown at the right as well as sepals, pistils and stamens, and at the bottom typical buds in various stages of opening.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June and July 2002 and 2003 at St. Paul, Minn., and May 2003 at Phoenix, Ariz.

Botanical classification: *Rosa hybrida,* var. 'BAIcker'.
Class: Landscape Shrub.
Plant:
- *Height.*—Approximately 60 cm on average at the end of the growing season.
- *Width.*—Approximately 80 cm on average at the end of the growing season.
- *Habit.*—Compact, upright, bushy, and oval to rounded.

Branches:
- *Color.*—Young stems: Yellow-Green Group 147B with Greyed-Purple Group 184B. Adult wood: Yellow-Green Group 146B.
- *Thorns.*—Size: commonly approximately 0.4 cm in length on average with prickles on the younger stems. Color: Greyed-Purple Group 185C.

Leaves:
- *Stipules.*—Generally parallel with the auricle facing outward.
- *Petioles.*—Upper surface: Yellow-Green Group 146C. Under surface: Yellow-Green Group 146C suffused with Greyed-Purple Group 184B.
- *Leaflets.*—Number: 3, 5 (most often), and 7. Shape: ovate with a rounded base and an acuminate tip. Serration: serrulate. Texture: bears a glossy finish and is physically firm. General appearance: medium green with a glossy surface when mature. Color (young foliage): Upper surface: Yellow-Green Group 146B blended with Greyed-Purple Group 184A and 184B. Under surface: Yellow-Green Group 146B blended with Greyed-Purple Group 184A and 184B. Color (adult foliage): Upper surface: Green Group 137A and 138A. Under surface: Green Group 138A.

Inflorescence:
- *Number of flowers.*—Commonly approximately 21 blooms on average per cluster on a lateral stem.
- *Peduncle.*—Yellow-Green Group 146A with highlights of Greyed-Purple Group 184B in coloration, and the length is approximately 1.0 cm on average.
- *Sepals.*—Upper surface: Yellow-Green Group 147B with some pubescence. Under surface: Yellow-Green Group 147A suffused with Greyed-Purple Group 185B. Size: approximately 2.75 cm in length on average.
- *Buds.*—Shape: generally pointed. Size: medium. Length: approximately 2.75 cm on average. Diameter: approximately 1.75 cm on average. Color: Upper petal surface: Red-Purple Group 60B blending to Red-Purple Group 61C to Yellow Group 1B. Under petal surface: Red-Purple Group 60A blending with highlights of Red-Purple Group 63C to Yellow Group 2C.
- *Flower.*—Shape: single. Diameter: approximately 7.5 cm on average. Color (when opening begins): Upper surface: Red-Purple Group 60A with highlights of Red-Purple Group 63B to Yellow Group 2D. Under surface: Red-Purple Group 65C suffused with Red-Purple Group 62A to Yellow Group 2C. Color (when blooming): Upper surface: Red-Purple Group 60A with highlights of Red-Purple Group 63B to Yellow Group 2D. Under surface: Red-Purple Group 64C with highlights of Red-Purple Group 64A and 64B to Yellow Group 11D. Color (at end of blooming): Upper surface: Red-Purple Group 63A. suffused with Red-Purple Group 60B to Yellow Group 11D. Under surface: Red-Purple Group 65D suffused with Red-Purple Group 63A to Red-Purple Group 63C to Yellow Group 11D. Color (basal petal spot): near white to Yellow Group 2D. Fragrance: slight rose. Lasting quality: the blossoms commonly last approximately 10 to 14 days on average depending upon the temperature and sunlight exposure. Petal number: approximately 10 under normal growing conditions. Petal shape: generally rounded. Petal drop: commonly the petals detach cleanly at full blossom maturity. Anthers: Yellow-Orange Group 17A. Filament number: commonly approximately 76 on average. Filament color: Yellow Group 13B. Pistils: approximately 27 on average. Stigmas: Yellow-Green Group 1B in coloration. Styles: Yellow Group 6A in coloration. Receptacle: separate and free. Hip shape: oval. Hip length: approximately 1.5 cm. Hip width: approximately 1.25 cm. Seeds: medium brown in coloration, and approximately 4.0 mm in length.

Development:
- *Vegetation.*—Vigorous, and compact.
- *Blooming.*—Heavy in June and on a recurrent bloom cycle thereafter.
- *Resistance to diseases.*—Excellent tolerance to Black Spot, and Powdery Mildew.
- *Hardiness zone.*—U.S.D.A. Hardiness Zone Nos. 4 to 9.

We claim:

1. A new and distinct variety of landscape shrub rose plant characterized by the following combination of characteristics:

(a) exhibits a compact, upright and bushy growth habit, (b) forms recurrently in clusters attractive rich medium red blossoms suffused with rosy pink having a near white to yellow eye, (c) forms glossy medium green adult foliage, (d) displays excellent tolerance to Black Spot and Powdery Mildew; and (e) is particularly well suited for growing as attractive ornamentation in parks and gardens;

substantially as herein shown and described.

* * * * *